(12) United States Patent
Jarvius et al.

(10) Patent No.: US 10,112,194 B2
(45) Date of Patent: Oct. 30, 2018

(54) DETECTION OF MICROSCOPIC OBJECTS

(71) Applicants: Jonas Sven Peter Jarvius, Uppsala (SE); Jan Grawe, Uppsala (SE)

(72) Inventors: Jonas Sven Peter Jarvius, Uppsala (SE); Jan Grawe, Uppsala (SE)

(73) Assignee: Q-linea AB, Uppsala (SE)

( * ) Notice: Subject to any disclaimer, the term of this patent is extended or adjusted under 35 U.S.C. 154(b) by 413 days.

(21) Appl. No.: 14/682,682

(22) Filed: Apr. 9, 2015

(65) Prior Publication Data

US 2015/0293270 A1    Oct. 15, 2015

Related U.S. Application Data

(60) Provisional application No. 61/979,319, filed on Apr. 14, 2014.

(51) Int. Cl.
*B01L 3/00* (2006.01)
*G02B 21/24* (2006.01)
*G02B 21/34* (2006.01)
*G02B 27/40* (2006.01)
*G01N 21/64* (2006.01)
*B29L 31/00* (2006.01)
*B29C 45/26* (2006.01)

(52) U.S. Cl.
CPC .... *B01L 3/502715* (2013.01); *G01N 21/6452* (2013.01); *G02B 21/241* (2013.01); *G02B 21/34* (2013.01); *G02B 27/40* (2013.01); *B01L 2200/025* (2013.01); *B01L 2300/0806* (2013.01); *B01L 2300/0851* (2013.01); *B29C 45/263* (2013.01); *B29L 2031/7728* (2013.01); *G01N 2021/6482* (2013.01)

(58) Field of Classification Search
CPC ......... B01L 2400/0409; B01L 2200/10; B01L 3/5025; B01L 3/5027; B01L 3/502707; B01L 3/50273; B01L 3/502746; B01L 3/502753; G01N 35/00069; G01N 2035/0441; G01N 21/01
See application file for complete search history.

(56) References Cited

U.S. PATENT DOCUMENTS

| | | |
|---|---|---|
| 4,883,867 A | 11/1989 | Lee et al. |
| 5,321,130 A | 6/1994 | Yue et al. |
| 5,410,030 A | 4/1995 | Yue et al. |
| 5,436,134 A | 7/1995 | Haugland et al. |
| 5,534,416 A | 7/1996 | Millard et al. |
| 5,582,977 A | 12/1996 | Yue et al. |
| 5,658,751 A | 8/1997 | Yue et al. |
| 5,863,753 A | 1/1999 | Haugland et al. |
| 5,871,921 A | 2/1999 | Landegren et al. |
| 6,558,928 B1 | 5/2003 | Landegren |

(Continued)

FOREIGN PATENT DOCUMENTS

| | | |
|---|---|---|
| GB | 1 321 123 | 6/1973 |
| WO | WO 2012/092238 A1 | 7/2012 |
| WO | WO 2012/160083 A1 | 11/2012 |

*Primary Examiner* — Sally A Merkling
(74) *Attorney, Agent, or Firm* — Fay Sharpe LLP

(57) ABSTRACT

A substrate for use in manufacture of a production master plate for production of a detection disc for carrying samples in an apparatus for detection of microscopic objects in a fluid, the substrate having a channel and separate focus structure, wherein the focus structure is a groove.

8 Claims, 6 Drawing Sheets

(56) References Cited

U.S. PATENT DOCUMENTS

| | | | |
|---|---|---|---|
| 6,835,293 B2 * | 12/2004 | Gerlach | B01L 3/5027 204/600 |
| 7,074,564 B2 | 7/2006 | Landegren | |
| 7,320,860 B2 | 1/2008 | Landegren et al. | |
| 7,545,496 B2 * | 6/2009 | Prins | B01L 3/502715 356/244 |
| 7,790,388 B2 | 9/2010 | Landegren et al. | |
| 7,889,615 B2 * | 2/2011 | Worthington | B01L 3/502715 369/100 |
| 8,003,926 B2 * | 8/2011 | Bedingham | B01L 3/5025 219/627 |
| 8,053,188 B2 | 11/2011 | Gullberg et al. | |
| RE44,265 E | 6/2013 | Landegren et al. | |
| 8,664,164 B2 | 3/2014 | Ericsson et al. | |
| 2008/0094974 A1 * | 4/2008 | Worthington | G01N 35/00069 369/53.2 |
| 2014/0030721 A1 | 1/2014 | Fredriksson et al. | |

* cited by examiner

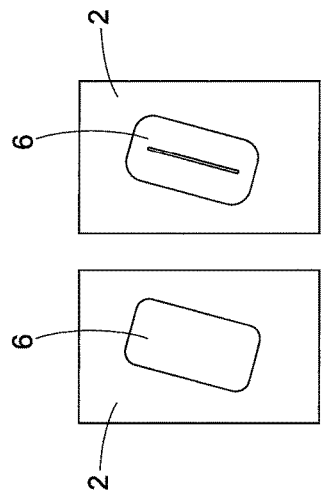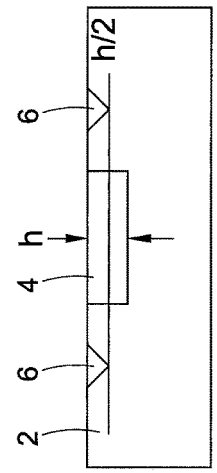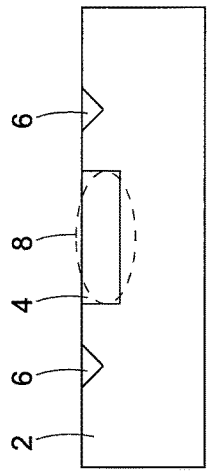
FIG. 4A    FIG. 4B
FIG. 5A    FIG. 5B
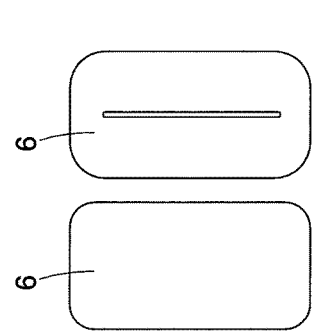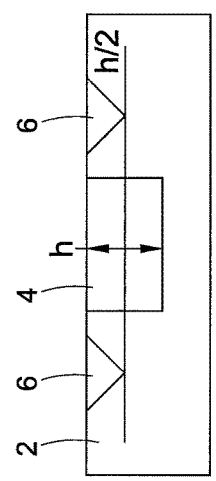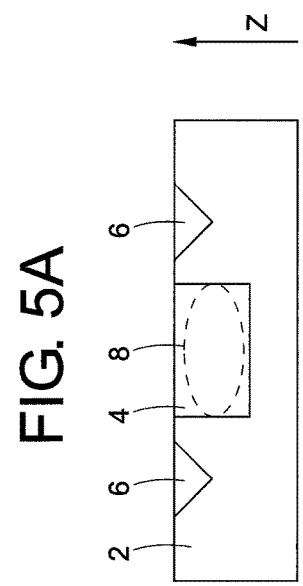
FIG. 7A    FIG. 7B

DETECTION OF MICROSCOPIC OBJECTS

This application claims the benefit of Provisional Application Ser. No. 61/979,319 which was filed on Apr. 14, 2014. The entire content of that application is incorporated hereinto by reference.

The present invention relates to detection of microscopic objects and to related products, apparatuses and methods.

It is important in many fields to be able to detect and/or count small objects such as bioparticles, molecules, cells and so on. One particular field where this is of use is in biotechnology, for example in relation to DNA replication/amplification, where it can be important to be able to detect molecular elements such as rolling circle products (RCPs).

One known system for detecting microscopic objects is flow cytometry. This is a laser-based, biophysical technology employed in cell counting, cell sorting, biomarker detection and protein engineering. Cells are suspended in a stream of fluid and passed by an electronic detection apparatus. Flow cytometry allows simultaneous multiparametric analysis of the physical and chemical characteristics of up to thousands of particles per second.

However, flow cytometry is not able to detect individual small objects at a microscopic scale, especially not in a sample of the type obtained by RCP production.

Flow cytometry is an example of a method that measures the integrated fluorescence within a defined volume, rather than the specific objects that may be contained within the volume. A particular problem arises for these methods when the label used for detection is also present in solution and not only associated with the object of interest. The presence of free labels in solution then easily overwhelms the signal from the object of interest. Another problem arises when the object of interest is very small, such as in single molecule detection methods. A key element to success is to improve signal over background and this is usually performed by reducing the investigated volume by various means. If the volume is small (<1 fL), background can be reduced to a minimum since it scales linearly with volume. The signal however does not change with decreased volume and thus signal over background is increased. This however causes an unreasonably long analysis time if a large volume, such as several microliters or even more several hundred of microliters or even milliliters of sample is to be investigated. Another solution to the problem is to image the fluorescence volume to be analysed with a resolution comparable to the size of objects to be detected. These can then be identified in the image as small areas of locally higher fluorescence intensity.

There is hence a need for new products, methods and apparatuses that would enable the detection and/or counting of single small objects, for example for single molecule detection in the context of RCPs.

Viewed from one aspect, the invention provides a substrate for use in manufacture of a production master plate for production of a detection disc for carrying samples in an apparatus for detection of microscopic objects in a fluid, the substrate having a channel and separate focus structure, wherein the focus structure is a groove.

To produce a functional structure comprising both a focus structure and a flow structure (also referred to as a channel, a flow channel or a detection channel) using a replication process, first the desired pattern may be transferred to a substrate, which may have a crystallographic structure. The substrate may comprise silicon. The substrate when processed may then be used to serve as a template of opposite polarity compared to a replication master (also referred to as a production master plate, or simply a master) used for production of the flow channel and focus structure. The replication process may for instance be thermoplastic injection moulding or casting. The production master plate may comprise nickel and may be produced by electroplating. The replication master may be used in CD-based thermoplastic injection moulding, to generate CD shaped substrates having the desired flow channel and focus structure. The focus structure is a groove in that it may have a cross-section that is constant along one primary direction of the focus structure, for example its length or width. The channel and groove may be provided in the (100) surface of the silicon. The focus structure is a groove in that it may have a cross-section that is constant along one primary direction of the focus structure, for example its length or width. The focus structure may have sloping {111}-oriented sidewalls. The focus structure may have a V-shaped cross-section. The focus structure may be oriented at right angles (that is, at 90 degrees) to the (110) plane. The channel may have a square or rectangular cross-section. Alternatively, the channel may have a U-shaped cross section, or may otherwise have a curved base such that the channel has an arc-shaped, inverted-arch-shaped or semi-circular shaped cross-section. The depth of the focus structure may be less than the depth of the channel. The depth of the focus structure may have a fixed (that is, predetermined, known in advance, or non-arbitrary) relationship with the depth of the channel. The depth of the channel may be twice the depth of the focus structure. Here, the depth of each of the focus structure and channel is taken to be the maximum depth, in cases where the depth varies across the cross-section of the focus structure or channel.

There may be multiple detection channels and multiple focus structures. The multiple detection channels may be arranged radially about a disc shape of the substrate, and wherein there may be at least one focus structure associated with each detection channel. In the instances where there are several channels on one disc, the channels may have different geometries and/or depths. The depth of the focus structure may have a predetermined relationship with the depth of the channel such that the same algorithms and optical settings can be used for every channel, independent of the geometry and/or depth of the channel. It is also possible to have independent or fixed offsets between the focal plane of the focus structure and the focal plane in the detection channel.

In another aspect, the invention provides a detection disc for carrying samples in an apparatus for detection of microscopic objects in a fluid, the detection disc having a detection channel and separate focus structure, wherein the focus structure is a groove, and wherein the detection disc is made using a production master plate manufactured using a substrate as described above. The invention also provides a detection disc for carrying samples in an apparatus for detection of microscopic objects in a fluid, the detection disc having a detection channel and separate focus structure, wherein the focus structure is a groove.

The disc may be made from a material with refractive index of greater than 1.22. The disc may be made from an optically transparent material. The disc may be made from a thermoplastic polymer. The disc may be made from a cyclo olefin polymer. The disc may be made from Zeonor® 1060R. The disc may be made from PDMS, UV-grade PMMA, PMMA, PC or a COC polymer-based material.

The focus structure is a groove in that it may have a cross-section that is constant along one primary direction of the focus structure, for example its length or width. The focus structure may have sloping sidewalls. The focus structure may have a V-shaped cross-section. The detection channel may have a square or rectangular cross-section. Alternatively, the channel may have a U-shaped cross section, or may otherwise have a curved base such that the channel has an arc-shaped, inverted-arch-shaped or semi-circular shaped cross-section. The depth of the focus structure may be less than the depth of the channel. The depth of the focus structure may have a fixed (that is, predetermined, known in advance, or non-arbitrary) relationship with the depth of the channel. The depth of the channel may be twice the depth of the focus structure. Here, the depth of each of the focus structure and channel is taken to be the maximum depth, in cases where the depth varies across the cross-section of the focus structure or channel.

The detection disc may have multiple detection channels and multiple focus structures. The multiple detection channels may be arranged radially about the disc, and wherein there may be at least one focus structure associated with each detection channel. In the instances where there are several channels on one disc, the channels may have different geometries and/or depths.

Viewed from a further aspect, the invention provides a method of manufacturing a substrate for manufacturing a master for a disc for carrying samples in an apparatus for detection of microscopic objects in a fluid, the substrate having a channel and separate focus structure, wherein the focus structure is a groove, the method comprising: providing the substrate having a crystallographic structure; forming the channel in the substrate with an orientation independent of the orientation of the crystalline planes; and forming the focus structure in the substrate with an orientation aligned with one of the crystalline planes.

The invention further extends to a method of manufacturing a master for a disc for carrying samples in an apparatus for detection of microscopic objects in a fluid, wherein the method of manufacture includes manufacturing a substrate as set out in the aspect described above, and using the substrate to manufacture a master.

The master may be manufactured from the substrate by electroplating. The master may be made of nickel.

The invention further extends to a method of manufacturing a disc for carrying samples in an apparatus for detection of microscopic objects in a fluid, wherein the method of manufacture includes manufacturing a substrate as set out in the aspect described above, using the substrate to manufacture a master, and using the master to manufacture the disc.

The disc may be manufactured from the master by injection moulding or casting.

The substrate may be silicon. The channel and focus structure may be etched into the (100) plane of the silicon. The focus structure may be etched along the {111} plane of the silicon. The focus structure may have a V-shaped cross-section. The channel may be etched to a depth D, and the focus structure may be etched to a depth that may be less than D. The depth of the focus structure may have a fixed (that is, predetermined, known in advance, or non-arbitrary) relationship with the depth of the channel. The focus structure may be etched to a depth of D/2.

Formation of the channel may be achieved using for instance the Bosch process or variants of the Bosch process, for example, DRIE dry etching. The focus structure may be formed using hydroxide etching, for instance using KOH, where, in silicon, the etch rate for the (110) plane is greater than the etch rate for the (100) plane, which is greater than the etch rate for the (111) plane. Therefore, a focus structure aligned with a crystalline axis can be formed.

Alternatively to KOH, TMAH (Tetramethylammonium hydroxide), EDP (Ethylenediamine Pyrocatechol), CsOH, NaOH or $N_2H_4$—$H_2O$ (Hydrazone) may be used. Depending on the desired depth of the focus structures an appropriate mask is chosen. For shallow structures (for example, with depth of less than 50 µm) $SiO_2$ is usually the simplest to use. For structures deeper than 50 µm one could chose $SiN_x$ as a mask.

The use of V-shaped focusing structures can be combined with rectangular shaped flow structures but it is not limited to be combined with this type of geometry for the flow structures. It is also possible to use the V-shaped focusing structures with arc-shaped flow or control channels and this could be beneficial especially if optical registration is to take place in the arch-shaped channel.

The substrate may be provided with features as described above.

A still further aspect provides a method of manufacturing a detection disc for carrying samples in an apparatus for detection of microscopic objects in a fluid, the detection disc comprising injection moulding the detection disc using a production master plate produced using the substrate as described above.

Another aspect provides a method of manufacturing a detection disc for carrying samples in an apparatus for detection of microscopic objects in a fluid, the method comprising: providing a substrate having a crystallographic substrate; forming the channel in the substrate with an orientation independent of the orientation of the crystalline planes; forming the focus structure in the substrate with an orientation aligned with one of the crystalline planes; using the substrate to produce a production plate; and using the production master plate to manufacture the detection disc having a detection channel and a focus structure.

The master may be produced by electroplating using the substrate as a template. The master may be made of nickel. The method may include forming a mould from the master; and injection moulding the detection disc using the mould in order to obtain a detection disc having a detection channel and a focus structure.

The focus structure may be formed to have a predetermined depth in relation to the depth of the channel. For example, the focus structure may have a depth that is related to the depth of the channel by a specific ratio.

This method may include providing the detection disc with features as described above.

A yet further aspect provides a method of finding a focus plane in an apparatus for detection of microscopic objects in a fluid, wherein the method comprises: providing an optically transparent substrate having a focus structure, the focus structure comprising a groove with sloping sidewalls provided in a first surface of the substrate; illuminating the substrate from a second surface, opposed to the first surface; imaging the focus structure on the first surface using an imaging apparatus, and focussing the imaging apparatus on the focus structure, wherein the angle between each sidewall of the focus structure and the first surface may be greater than the critical angle of the substrate.

The focus structure is a groove in that it may have a cross-section that is constant along one primary direction of the focus structure, for example its length or width. The focus structure may have a V-shaped cross-section. The method may include using information about the focus plane found by the imaging apparatus to focus a further, separate, imaging apparatus to the same focus plane. The focussing imaging apparatus may be an area detector and the further imaging apparatus may be a line detector. The method may comprise illuminating the detection channel with a line beam, the projection of the line beam being co-linear to the line of the line detector at the imaging plane.

The substrate may be a detection disc as described above and the focus structure may be a focus structure of the disc.

A further aspect provides a method of focussing a first imaging apparatus to a focus plane in an apparatus for detection of microscopic objects in a fluid, wherein the method comprises: imaging a focus structure with a second imaging apparatus, focussing the second imaging apparatus on the focus structure to find the focal plane; and focussing the first imaging apparatus to the focal plane to which the second imaging apparatus is focussed. The first imaging apparatus may be a line detector, and the second imaging apparatus may be an area detector. Alternatively, an area detector is used as the first imaging apparatus where a selected line or a selected subset of lines can be read out, e.g. a CMOS array. Alternatively, a single line detector serves the purpose of both the first and second imaging apparatus. Alternatively, a single imaging apparatus where a selected line or a selected subset of lines can be read out, e.g. a CMOS array, serves the purpose of both the first and second imaging apparatus.

The focus structure is a groove in that it may have a cross-section that is constant along one primary direction of the focus structure, for example its length or width. The focus structure may comprise a groove with sloping sidewalls provided in a first surface of the substrate, wherein the angle between each sidewall of the focus structure and the first surface may be greater than the critical angle of the substrate. The method may comprise illuminating the detection channel with a line beam, the projection of the line beam being co-linear to the line of the line detector at the imaging plane. The line of the line detector and the projection of the line beam may both be perpendicular to the channel. The method may comprise using a detection disc as described above, where the focus structure is a focus structure of the disc.

In another aspect, the invention provides an apparatus for detecting and/or counting microscopic objects comprising: a detection disc comprising a detection channel for carrying the microscopic objects in a sample fluid and a separate focus structure associated with the detection channel, a first imaging apparatus for finding a focal plane by focussing on the focus structure; a second imaging apparatus for detecting and/or counting the objects in the detection channel, the second imaging apparatus being focussed to the focal plane using information about the focal plane from the first imaging apparatus. The first imaging apparatus may be a line detector, and the second imaging apparatus may be an area detector. Alternatively, an area detector is used as the first imaging apparatus where a selected line or a selected subset of lines can be read out, e.g. a CMOS architecture. Alternatively, a single line detector serves the purpose of both the first and second imaging apparatus. Alternatively, a single imaging apparatus where a selected line or a selected subset of lines can be read out, e.g. a CMOS array, serves the purpose of both the first and second imaging apparatus.

The focus structure is a groove in that it may have a cross-section that is constant along one primary direction of the focus structure, for example its length or width. The focus structure may comprise a groove with sloping sidewalls provided in a first surface of the substrate, and wherein the angle between each sidewall of the focus structure and the first surface may be greater than the critical angle of the substrate. The apparatus may include a light source for illuminating the detection channel with a line beam, the projection of the line beam being co-linear to the line of the line detector at the imaging plane. The line of the line detector and the projection of the line beam may both be perpendicular to the channel. The detection disc may be as described above.

A further aspect of the invention provides an apparatus for detecting and/or counting microscopic objects, the apparatus comprising: a detection disc comprising a detection channel for carrying the microscopic objects in a sample fluid and a separate focus structure associated with the detection channel,
a first imaging apparatus for finding a focal plane by focussing on the focus structure; a second imaging apparatus for counting the objects in a detection channel, the second imaging apparatus being focussed to the focal plane using information about the focal plane from the first imaging apparatus, wherein the focus structure comprises a groove with sloping sidewalls provided in a first surface of the detection disc, and wherein the angle between each sidewall of the focus structure and the first surface is greater than the critical angle of the substrate.

The focus structure is a groove in that it may have a cross-section that is constant along one primary direction of the focus structure, for example its length or width. The focus structure may have a V-shaped cross-section. The apparatus may comprise a further, separate, imaging apparatus that receives information about the focal plane found by the focussing imaging apparatus and uses this information to focus on the focal plane. The focussing imaging apparatus may be an area detector and the further imaging apparatus may be a line detector. Alternatively, an area detector is used as the first imaging apparatus where a selected line or a selected subset of lines can be read out, e.g. a CMOS architecture. Alternatively, a single line detector serves the purpose of both the first and second imaging apparatus. Alternatively, a single imaging apparatus where a selected line or a selected subset of lines can be read out, e.g. a CMOS array, serves the purpose of both the first and second imaging apparatus.

The apparatus may include a light source for illuminating the detection channel with a line beam, the projection of the line beam being co-linear to the line of the line detector at the imaging plane. The line of the line detector and the projection of the line beam may both be perpendicular to the channel.

The detection disc may be as described above.

A still further aspect of the invention provides a sample processing module for an apparatus for detecting and/or counting microscopic objects, the sample processing module comprising: a carousel for holding a plurality of sample containers; a number of stations for sample processing steps including a filling station for filling the sample containers, a heating station for heating a sample in the sample container; a cooling station for cooling the sample in the sample container; an agitation station for agitating the sample in the sample container; and a purging station for purging the sample from the sample container and passing it to a detection module for analysis of the sample; wherein the heating and cooling stations act on the sample without contact with the sample.

The heating station may use infra-red or heated air to heat the sample. Each of the filling, heating, cooling and purging stations may act without contact between the stations and the sample container held in the carousel.

The filling station may comprise a dispensing nozzle arranged to fill the sample container without contact with the container or carousel. The purging station may comprise a compressed air source arranged to expel the sample through a hole in the container without contact between the compressed air source and the container or carousel.

The sample processing module may be used in conjunction with the apparatus of any of the other aspects described above.

Certain preferred embodiments are described below by way of example only and with reference to the accompanying figures in which:

FIGS. 4A and 4B show a schematic and a photograph respectively with, on the left, an out of focus image and, on the right, a focussed image of the focus structure;

FIGS. 5A and 5B show two schematic cross-sections with the detection channel and focus structures for two example depths of channel;

Figure 1:
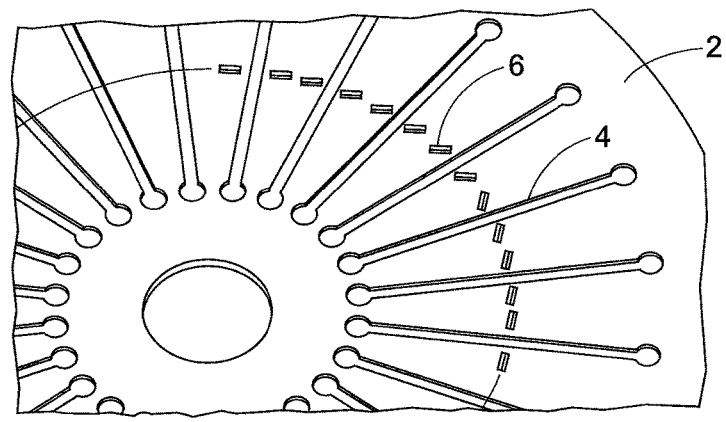
FIG. 1 shows a part of a moulded disc with detection channels and focus structures, the focus structures being shown with exaggerated size for illustrative purposes.
Figure 2:
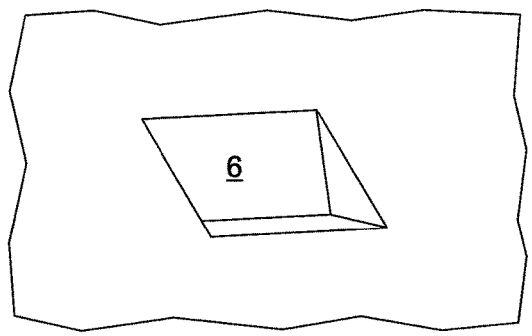
FIG. 2 shows a focus structure in close up view.
Figure 8:
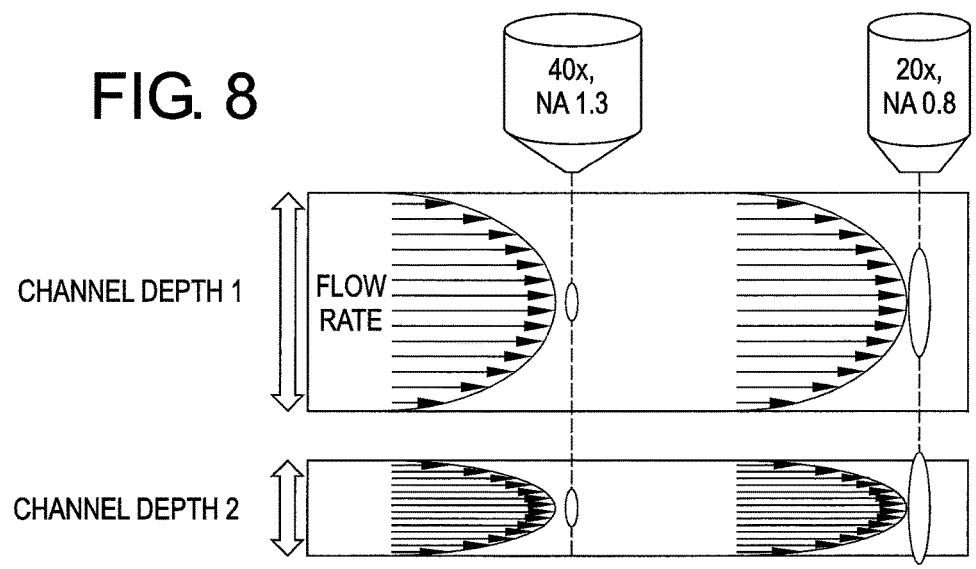
Figure 9:
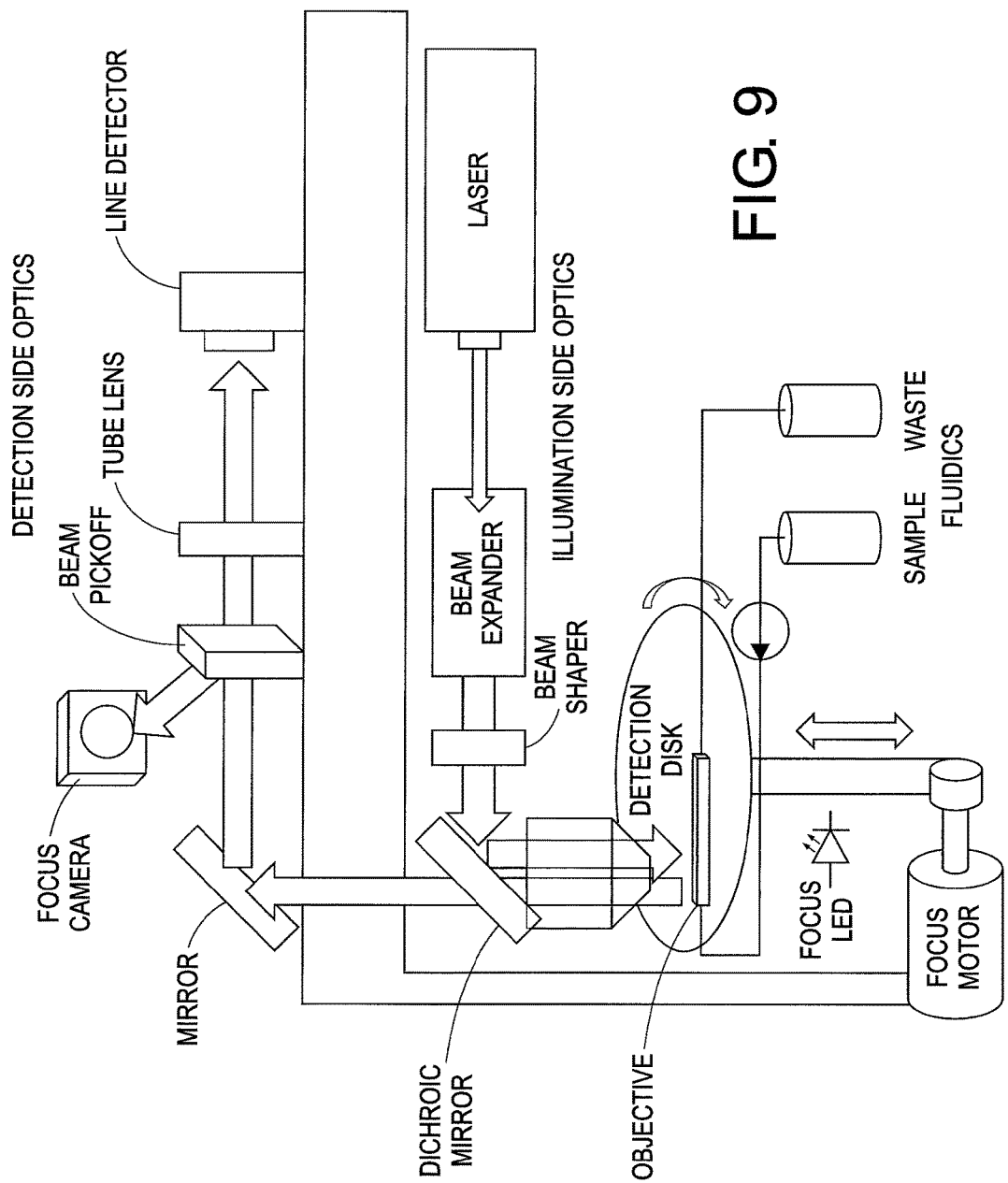
Figures 10A, 10B:
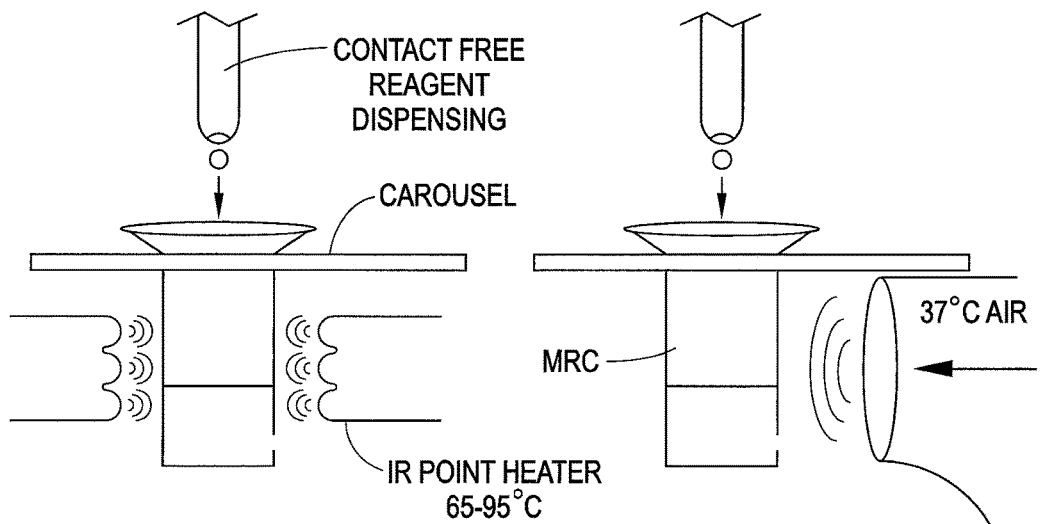
Figure 11:
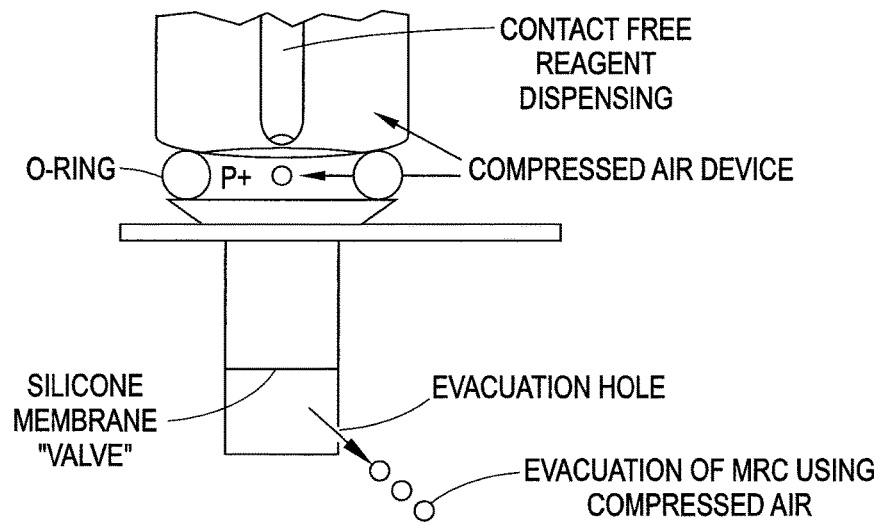

FIGS. 7A and 7B respectively illustrate correct and incorrect matching of the optical sampling volume to the channel geometry;

FIG. 8 shows flow rate of the sample fluid across the width of a detection channel;

FIG. 9 shows an example apparatus using high speed fluorescence detection to detect objects in the detection channels of a disc of the type shown in FIG. 1;

FIGS. 10A and 10B show non-contact heating used in a sample processing module of an example apparatus; and FIG. 11 shows purging of a microfluidic reaction container in the sample processing module.

Figure 12:
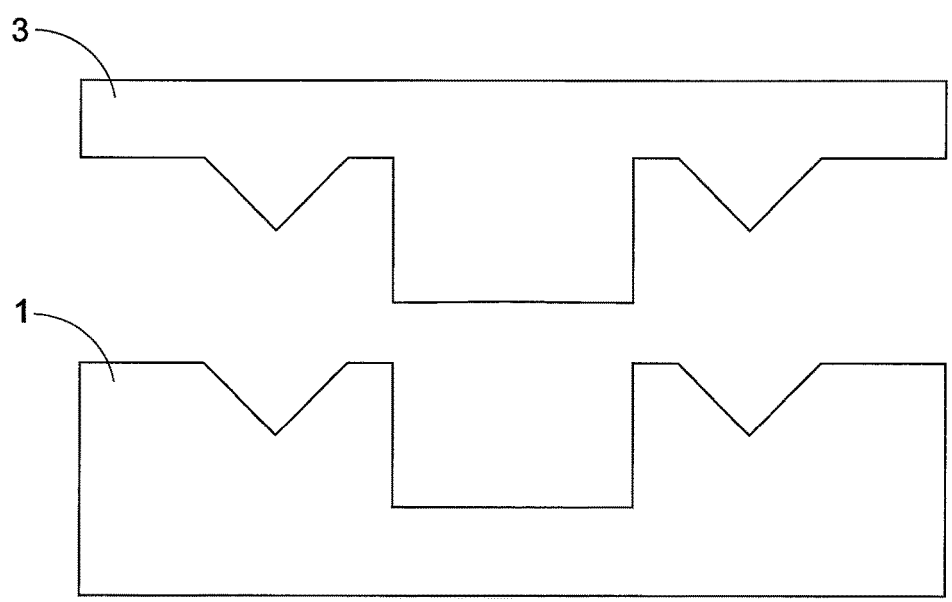

FIG. 12 shows the relation between the substrate having a crystallographic structure and the production master.

This disclosure concerns an apparatus for detecting of and counting of microscopic objects, such as particles (particularly bio-particles), cells, micro-organisms such as bacteria or molecules including macromolecules. The microscopic objects can include any object that is suitable small in size and can be detected based on optical methods, in particular fluorescence of the object or of a fluorescent composition applied to the object. If the objects are translucent objects without scattering properties, such as RCPs, the objects may be 10 µm or less in size, perhaps 5 µm in size or smaller. The objects may have a largest dimension of 2 µm or less, perhaps 1.5 µm or less, 1 µm or less and in some cases 0.5 µm or less.

The example apparatus of the preferred embodiment uses optical elements to detect small objects in a detection channel 4 of a sample substrate 2 in the form of a disc 2. FIG. 1 shows a part of the disc 2. The disc 2 has multiple such detection channels 4 and can be rotated to allow repeated testing or different tests during a single test cycle. FIG. 1 shows a disc with the same geometry for each channel 4 but the channel geometry could be varied on a single disc to allow different tests to be performed. The disc 2 also includes a focus structure 6, explained in more detail below. The focus structure 6 is used to determine a focus depth for best detection of small objects in a fluid in the detecting channel 4. Each detection channel has adjacent focus structures 6.

The focussing uses a dedicated focussing camera and it is carried out automatically as a part of the test cycle for the apparatus. The focussing camera may be a CCD area imaging chip. It is an area camera, i.e. a camera that captures a two dimensional image. Focussing may be carried out by a suitable algorithm. One algorithm is explained below. The focus information obtained by the focussing camera is used to set the focus depth for a line camera that detects the small objects in the detection channel 4. This line detector may be any suitable line camera, such as a CCD linear sensor and the use of the line detector is discussed in more detail below. The output from the line detector is an image allowing counting of the small objects of interest. Advantageously, by the use of the proposed focus structure and detection channel it becomes possible to automatically focus accurately onto a text volume that is small enough for single small objects, such as single molecules to be detected and counted. The apparatus can hence be used for single molecule detection, for example in relation to rolling circle products (RCPs) generated during DNA replication/amplification.

The processes used to generate the samples for the apparatus may be conventional process for production of samples of RCPs, bacteria, cells, macro-molecules or any other microscopic object requiring detecting and/or counting. Possible processes that might be used to provide samples for use with the proposed new apparatus are described in [earlier patent publications. Of special interest are processes generating Rolling Circle Products as a result of detection of nucleic acids, proteins, cellular or other macromolecular targets via the use of so called Padlock probes, Proximity ligation, Proximity Extension or methods for circularization of nucleic acids as described in e.g. U.S. Pat. No. 7,790,388, U.S. Pat. No. 8,053,188, U.S. Pat. No. 7,320,860, RE44265, U.S. Pat. No. 7,074,564, U.S. Pat. No. 5,871,921, U.S. Pat. No. 6,558,928, U.S. Pat. No. 8,664,164, US20140030721 or WO2012160083. One example process that could be used to generate samples in the form of RCPs is described in the applicant's co-pending patent application GB 1321123.0. Fluorescent labelling of bacteria is well known in the art. Examples include the use of non-specific detection protocols that employ signal producing systems that stain the double stranded DNA of bacteria, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. The nucleic acid stain may be or may incorporate an acridine dye, or a homo- or heterodimer thereof, such as acridine orange, acridine homodimer, ethidium-acridine heterodimer, or 9-amino-6-chloro-2-methoxyacridine. The nucleic acid stain may be an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating Tb3+ and Eu3+, for example). The nucleic acid stain may be a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR, SYTO, SYTOX, PICOGREEN, OLI-GREEN, and RIBOGREEN from Molecular Probes, Inc., Eugene, Oreg. The nucleic acid stain may be a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

Other methods of staining bacteria utilizes stains that distinguish live from dead bacteria such as is described in e.g. U.S. Pat. No. 5,534,416 or WO 2012092238.

Advantageously, the samples may be processed automatically using a sample preparation module (SPM) provided as part of the detection apparatus. The SPM may automatically prepare the samples as discussed in more detail below.

Focus Structure

The focus structure 6 is placed just beside the detection channel 4 and is used as a surrogate marker. A dedicated focusing camera focusses on the focus structure 6 instead of focusing directly on the objects to be detected. An advantage of this is that no fluorescence signal is needed for focusing, focusing is not dependent on the objects being in a fixed position, and focusing is always made at a fixed depth, defined by the geometry and depth of the focus structure 6. The depth of the focus marker can be placed at any depth in relation to the depth of the detection channel, as will be seen from the discussion below the focus marker may have a depth that is a half of the depth of the detection channel.

The focus structure consists of a V-shaped groove in the moulded disc. The disc is manufactured by injection moulding using a production master (reference numeral 3 in FIG. 12) in e.g. nickel produced from a silicon substrate (a wafer of silicon, reference numeral 1 in FIG. 12). This process is similar to the processes used for manufacture of compact discs as used for storage of data and music. In fact a CD moulding machine may be used to create the discs.

To produce a functional structure comprising both a focus structure and a flow structure using a replication process, first the desired pattern is transferred to a substrate having a crystallographic structure. The substrate may comprise silicon. The substrate when processed is then used to serve as a template of opposite polarity as a replication master (production master plate, or master) used for production of the flow and focus structures. The replication process can for instance be thermoplastic injection moulding or casting. The production master plate may comprise nickel and may be produced by electroplating. In one preferred embodiment the replication master is used in CD-based thermoplastic injection moulding, to generate CD shaped substrates having the desired flow and focus structures as described above.

In the silicon substrate, the shape of the flow channels (also referred to as detection channels) are etched independent of the orientation of the crystal axes in the silicon substrate using deep reactive-ion etching (DRIE). The shape of the focus structure (V-groove) is etched along the (111) plane of the crystal wafer. The angle between the surface of the master and the (111) plane is then 54.7 degrees.

The focus structure is etched by wet etching as described above, with e.g. potassium hydroxide (KOH). The depth of the focusing structure is defined by the diameter of opening in the mask used for wet etching, such that it possible to define structures of different depth and to correlate those with the depth of the flow channels. The depth of the focussing structure is set to be less that the depth of the flow channel. In the examples shown in FIGS. 5A and 5B, the depth of the flow channel is h, and the depth of the focus structure is h/2 (i.e. half the depth of the flow channel). The same focusing strategy can then be used independent of the depth of the flow channel. The focussing camera can obtain good information about the focus depth even if the height and position of the disc is not constant for different discs or for different detection channels on the same disc. There is always a focus reference point adjacent to the detection channel that provides an accurate focus depth for the channel of interest. It should be noted that the relationship between focus structure depth and the detection channel depth can be set at a predetermined off-set to each other.

Since the silicon plane is used to wet-etch the focus structures they can only be oriented in 90 degree angles from the top plane. This is not the case for the DRIE etched flow channels, which are placed radially along the disc. The combination of the two etching techniques generates an optimal system to deliver both a focusing structure defined by the crystal plane and an arbitrarily-oriented but rectangular-shaped flow channel.

The materials used to manufacture the injection-moulded disc may be Zeonor® 1060R with a refractive index of 1.5, or PDMS (refractive index 1.4). The refractive index of the disc material should be greater than about 1.22 (1/sin(54.7)), for reasons explained below. Other suitable materials can of course also be used for the detection disc such as UV-grade-PMMA, PMMA, PC or other COC polymer based materials. In order to have as sharp focusing structures as possible it is preferable to use thermoplastic materials with excellent form-filling and flow characteristics.

Figure 3A:
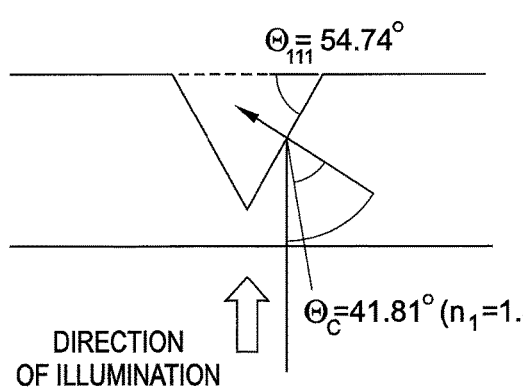
FIGS. 3A and 3B illustrate a light beam directed at the focus structure and the resultant reflection and refraction of light rays.
Figure 3B:
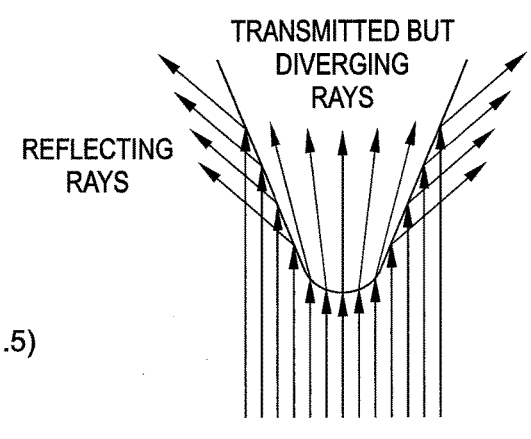

When focusing, the grove is illuminated from below with a light beam, close to parallel, as shown in FIG. 3A. As can be seen from FIG. 3B, the incident angle of a collimated light beam on the sidewalls of the groove gives rise to total reflection when the refractive index of the disc material is greater than about 1.22 (i.e. 1/sin(54.7), where 54.7 is the angle between the surface of the master and the (111) planes). In the case of a less than perfectly collimated beam, the reflection may not be total, but sufficient for contrast detection as detailed below.

As a result of the total internal reflection, when viewed from the top, the area of the groove appears dark. If the imaging camera is focused exactly on the bottom level of the groove, where the sidewalls of the V-shaped groove meet, a bright line appears. The contrast between this bright line and the dark surrounding changes rapidly with changing focus plane, allowing precise contrast-based focusing. In each of FIGS. 4A and 4B (which show corresponding view, as a schematic in FIG. 4A, and as a photograph in FIG. 4B), the figure on the left shows the view when the imaging camera is out of focus, and the figure on the right shows the view when the imaging camera is in focus.

Focusing Algorithm

The focus plane of the image used for autofocus is first placed at a known position relative to the position of the bottom of the groove. That is, it is known that the groove will not be in focus, but the position is close enough so the dark area of the entire groove can be identified. Also, it is known whether the actual focus position is on the far or near side of the groove bottom.

First the algorithm finds the dark area of the groove, and masks this. Then, using a pre-defined threshold, the algorithm tries to find a lighter area contained within the dark area. If it succeeds, a contrast value is calculated. The algorithm then moves the focal plane a defined step size closer to the groove bottom, the procedure is repeated, and as long as the contrast value increased, the algorithm moves in the same direction. When a contrast value smaller than the previous is calculated, the direction of movement is reversed, and the step size is halved. This continues until a max focus value using the smallest step size possible is reached. The groove bottom is then focused to within less than 1 µm, or even within less than 0.5 µm. The invention thus provides a production method and a design of a focus structure enabling more precise focussing using a very simple algorithm than existing other means of producing a substrate to be used for autofocussing of a sample. One of the key features of the invention is the production of the focus structure in the same material as the detection channel and possibly at the same time. No additional work that can affect the positioning of the focus structure in relation to the focus volume in the detection channel needs to be performed afterwards. Such as is the case using e.g. metal markers attached to a surface as is used in existing solutions. The positioning within less than 1 µm of the wanted focus plane of the current invention is superior in precision compared to current methods relying solely on reflection.

Line Detector

A sample volume in the detection channel is imaged with a line detector (a line camera having a single line of pixels).

The different images that would be obtained for a given line rate are shown in FIGS. 6A to 6D, which show in the top drawings the particles moving through the channel, and in the bottom drawings, the image obtained by the line camera. The image obtained is built up of a large number of lines.

Figures 6A, 6B, 6C, 6D:
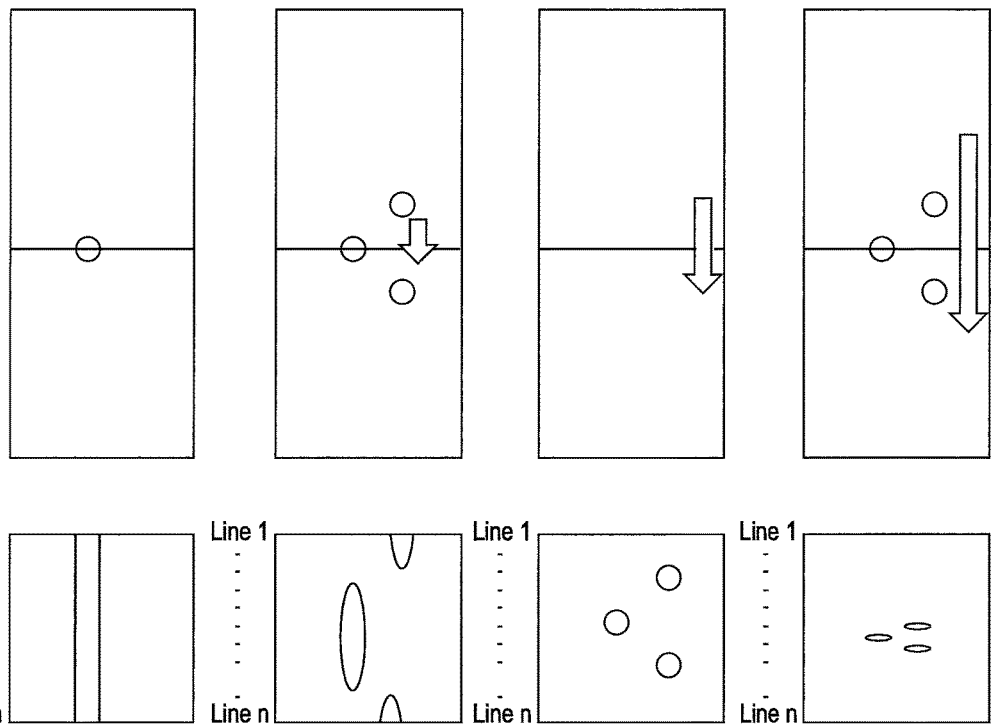
FIGS. 6A-6D illustrate images of objects in a detection channel, the images taken with different line rates of a line camera in each of FIGS. 6A, 6B, 6C and 6D.

In FIG. 6A, the object is stationary, and all lines are identical. When the object moves slowly (as in FIG. 6B), the line image will change slowly. When the object moves in sync with the rate of line images taken (as in FIG. 6C), the frame accurately reproduces the object. When the object moves faster (as in FIG. 6D), the objects appears compressed, in the extreme case to single short lines.

The sample fluid that is pumped through the detection channel has a parabolic flow rate over the channel width (see FIG. 8). The line rate of the detector, while variable, is the same over the whole line image. It is therefore not possible to achieve a 1:1 ratio between flow rate and the line rate (as in FIG. 6C) over the entire channel width. However this is not necessary when counting the number of microscopic particles (for example, RCPs). By adjusting the flow and line rate it is possible to compress the 2D image of a particle into one single exposure of the line detector. It will then become a line of a certain width. This is done for a certain region of interest (ROI) of the channel, excluding the areas adjacent to the channel sides.

The advantage of compressing the image in this way is that the intensity of the pixels containing then object is strongly elevated over the background compared to 1:1 imaging. Furthermore, the image analysis speed increases. The image size needed to record a given volume of fluid also decreases. Finally, only very large objects falling within the ROI will cover more than 1 line, and can be readily rejected as artefacts.

Optical Sampling Volume

The optical sampling volume should be matched to the channel geometry. FIG. 7A illustrates a matched setup, in which the entirety of the optical sampling volume is contained within the sample volume (i.e. within the cross-section of the detection channel). FIG. 7B illustrates a mismatch, wherein the optical sampling volume is not entirely contained within the sample volume. This will lead to unwanted reflections and other artefacts relating to the channel top and bottom being included in the optical observation volume.

It is also clear from FIGS. 7A and 7B that the effect of channel drift in the z-axis is minimized using a deeper channel as smaller drifts will still keep the observation volume within the channel. If a shallow channel is used, any drift will sooner place the observation volume outside the channel.

The voxel in which an RCP will be imaged as a point is limited by the optical resolution in the axial direction, and (depending on pixel size, numerical aperture and magnification, and flow rate) either the optical lateral resolution, the pixel size, or the flow rate. First, if the flow rate is disregarded (or set to 0), the lateral resolution using a 40×, MN1.3 objective with an excitation wavelength of 532 nm is 0.23 µm, and for a 20× NA 0.8 objective 0.38 µm, according to Equation 1.

$$FWHM_{Ill,lateral} = 0.51 \frac{\lambda_{exc}}{NA} \quad \text{Equation 1}$$

Here, NA is the numerical aperture of the objective and $\lambda_{exc}$ is the wavelength of the excitation light.

In the image plane, the projected distance is 9.05 or 7.65 µm for 40 and 20× objectives, respectively. The pixel width of the line detector is 14 µm. A typical RCP has a diameter of 0.5 µm, but can be around 1 µm, or e.g. 1.5 µm. RCPs can also be of larger size, e.g. 10 µm, 5 µm or 2.5 µm if using additional amplification of the object on the primary RCP. RCPs have the unusual property compared to many other objects of similar size that they do not have scattering properties. This translates in the image plane to 20 µm for a 40× and 10 µm for a 20× objective. Thus, when imaging an RCP the lateral resolution is limited by the pixel size so that a typical RCP covers about 2 pixels using 40× and 1 pixel using a 20× objective.

Conversely, the pixel sizes projected onto the object plane are 0.35 and 0.7 µm for the 40 and 20× objectives.

With regard to axial resolution, this is described by Equation 2

$$FWHM_{det,axial} = \sqrt{\left(\frac{0.88 \cdot \lambda_{em}}{n - \sqrt{n^2 - NA^2}}\right)^2 + \left(\frac{\sqrt{2} \cdot n \cdot PH}{NA}\right)^2} \quad \text{Equation 2}$$

Here, $\lambda_{em}$ is the emission wavelength, PH is the object-side pinhole diameter (in µm), n is the refractive index of the immersion liquid (the fluid in which the objects to be counted are carried) and NA is the numerical aperture of the objective.

Here, the height of the CCD pixel line, as a virtual slit, is used as pinhole size, 28 µm. It should be noted that this value is higher than the pinhole diameter required for optimum confocality (pinhole size=1 Airy unit), which is 20 µm for a 40× NA 1.3 objective, and 16 µm for a 20× 0.8 NA objective. This is in line with the main purpose of the design, namely to minimize the influence if fluorescence related to unbound detection fluorophores present throughout the channel. In the present configuration, the 28 µm slit height represents a balance between background rejection and signal loss.

Using eq. 2, the axial FWHM is 2.4 µm and 7.8 µm for 40× NA 1.3 and 20× NA 0.8 um, respectively. Thus, using a 40× 1.3 NA objective a voxel in the object plane is about 0.35×0.35×2.4 µm for the 40×, and 0.7×0.7×7.8 µm for the 20× objective.

When using a channel of a fixed height, the choice of these objectives affects the properties of the analysis. With the 40× objective the voxel depth is significantly smaller than for the 20×. Thus, a smaller portion of the channel depth is scanned.

When the focal plane is centred in the mid-channel, (see FIG. 8) the flow rate variation over the voxel height and artefacts related to the channel top and bottom are minimal. This translates into a more homogenous volume to be analysed, and in turn a greater counting precision. Using the 20×, on the other hand results in a larger portion of the channel being scanned at the cost of a certain precision loss.

The flow rate in the system is adjustable between 5 and 50 µl/minute. A common value is 25 µl/min. Using a channel with a 60×400 µm cross-section, the average flow velocity is then 17400 µm/second. The line rate of the cameras is 5 kHz. The average movement of the fluid per exposure is then about 3.5 µm. The pixel height projected onto the object plane is 1.4 µm if a 20× objective is used. Therefore, a standard RCP of about 0.5 µm diameter will completely pass the detector line in one exposure, giving a 1D representation of the fluorescence intensity profile. In the above calculation, an average speed across the channel is assumed, although this is of course a simplification.

High-Fluorescence Detection of RCPs

One use for the apparatus is detection of RCPs. Solutions containing the labelled RCPs are analysed using a dedicated high-speed fluorescence detection instrument as shown in FIG. 9. The sample solution is pushed through a flow channel with a cross section of 200×40 µm (WxH). The flow channels are aligned radially on a CD-format plastic disc as described above, with appropriate optically clear lid and fluid interfaces, allowing rapid change of channel in case of a malfunction or clog.

Three lasers with wavelengths of 488 nm (Calypso, 100 mW, Cobolt AB, Solna, Sweden), 532 nm (Samba 300 mW, Cobolt AB, and 640 nm (Cube 640, 40 mW, Coherent Inc, Santa Clara, Calif.), are collimated through individually focusable beam expanders, bringing the beam diameters up to about 8 mm (1/e2). The beams are made collinear by a system of steerable dichroic and full mirrors. The collinear beams passed through a beam shaping lens, designed to produce in conjunction with a high numerical objective (Zeiss Fluar 40×, NA 1.3, Carl Zeiss AB, Stockholm, Sweden), a line illumination profile across the interrogation volume of the flow channel. Finally, just prior to the objective entrance pupil, the laser light passes through a laser-pass dichroic mirror (Semrock Inc, Rochester, N.Y.).

Fluorescent light is emitted by RCPs pumped across the interrogation volume using a syringe pump (Tecan XLP6000, Tecan Nordic AB, Molndal, Sweden). The emitted wavelength(s) corresponds to the emission spectra of the fluorescent labels bound to RCPs. The emitted light is collected through the objective is reflected or passes through the dichroic mirror, and is further collected by CCD line detectors (DALSA Spyder 3, 1024 pixels, line rate 5 kHz, Parameter AB, Stockholm, Sweden). Dichroic mirrors and band-pass filters are used to direct the light from each specific fluorophore to a specific detector. A small portion of the fluorescent light is redirected by a beam sampler onto a CCD area detector (µEye UI-1545LE-M, Parameter AB, Stockholm, Sweden) in order to allow for channel alignment and focusing.

From each detector the results of each sample run are registered as a series of x-t images where each RCP is identified through image analysis. The image analysis consists of background subtraction, pattern recognition, pattern matching across detectors for multiply fluorescent objects discrimination of RCPs and non-specific events, and RCP counting. For each reagent, a threshold for the number of RCPs is set to designate a positive sample.

It will of course be appreciated that this example method can be adapted for use with small objects other than RCPs. Possible small objects that can be detected and counted by the proposed apparatus are discussed above.

Sample Preparation Module

The Sample Processing Module (SPM) in this example accepts as a sample either nucleic acid targets to be interrogated, or templated nucleic acid circles created via well-known methods such as immuno-RCA or proximity ligation, indicating target proteins. Of course, other small objects as mentioned above could be used as the sample without departing from the main concepts described herein.

The SPM comprises a carousel for holding the samples. The carousel is advanced one step every minute and a new sample can be accepted as rapidly as every 4th minute. If a sample is to be processed, a sample container (microfluidic reaction container, MRC) is inserted into the carousel, and stepwise transported and processed through the circle.

At certain positions, reagents are dispensed, the MRC is heated, cooled, agitated or purged through a simple, integrated valve.

All reactions such as dispensing, heating, cooling, agitation, and purging are done in a contact-free manner (as shown in FIGS. 10A, 10B and 11), and the only contact with the processed sample is at the very end of the process where the sample is aspirated to a detection module (DM) for readout.

The described SPM has the following advantages:
1) sample throughput of 100+ samples per day without refill of reagents or consumables;
2) rate of analysis up to 1 sample/5 minutes;
3) random access;
4) minimal risk of cross-contamination between samples; and
5) small footprint and low weight.

The process carried out by the SPM can be any known process for preparation of samples for detection. Compared to known devices, the SPM differs in that the reactions and in particular the heating are carried out without contact.

The following clauses set out features of the invention which may not presently be claimed in this application, but which may form the basis for future claims, amendment or divisional applications.

Several embodiments of the disclosure will be discussed in the numbered paragraphs entitled "Clauses" set forth below.

Clauses

1. A substrate for use in manufacture of a production master plate for production of a detection disc for carrying samples in an apparatus for detection of microscopic objects in a fluid, the substrate having a channel and separate focus structure, wherein the focus structure is a groove.
2. A substrate according to clause 1, wherein the substrate comprises a material having a crystallographic structure.
3. A substrate according to clause 2, wherein the substrate comprises silicon.
4. A substrate according to clause 3, wherein the channel and groove are provided in the (100) surface of the silicon.
5. A substrate according to clause 4 wherein the focus structure has sloping {111}-oriented sidewalls.
6. A substrate according to any preceding clause wherein the focus structure has a V-shaped cross-section.
7. A substrate according to clause 4, 5 or 6 wherein the focus structure is oriented at right angles to the (110) plane.
8. A substrate according to any preceding clause, wherein the channel has a square or rectangular cross-section.
9. A substrate according to any preceding clause, wherein the channel has a U-shaped cross section, or may otherwise have a curved base such that the channel has an arc-shaped, inverted-arch-shaped or semi-circular shaped cross-section.
10. A substrate according to any preceding clause, wherein the depth of the focus structure is less than the depth of the channel.
11. A substrate according to any preceding clause, wherein the depth of the focus structure is at a predetermined depth in relation to the channel depth.
12. A substrate according to any preceding clause, wherein the depth of the channel is twice the depth of the focus structure.
13. A substrate according to any preceding clause, comprising multiple detection channels and multiple focus structures.
14. A substrate according to clause 13, wherein the multiple detection channels are arranged radially about a disc shape of the substrate, and wherein there is at least one focus structure associated with each detection channel.
15. A detection disc for carrying samples in an apparatus for detection of microscopic objects in a fluid, the detection disc having a detection channel and separate focus structure, and wherein the focus structure is a groove, wherein the detection disc is made using a production master plate manufactured using the substrate of any preceding clause.
16. A detection disc for carrying samples in an apparatus for detection of microscopic objects in a fluid, the detection disc having a detection channel and separate focus structure, wherein the focus structure is a groove.
17. A detection disc according to clause 15 or 16, wherein the disc is made from a material with refractive index of greater than 1.22.
18. A detection disc according to any of clauses 15 to 17, wherein the disc is made from an optically transparent material.
19. A detection disc according to any of clauses 15 to 18, wherein the disc is made from a thermoplastic polymer.
20. A detection disc according to clause 19, wherein the disc is made from a cyclo olefin polymer.
21. A detection disc according to clause 20, wherein the disc is made from Zeonor® 1060R.
22. A detection disc according to any of clauses 15 to 19 wherein the disc is made from PDMS, UV-grade PMMA, PMMA, PC or a COC polymer-based material.
23. A detection disc according to any of clauses 15 to 22 wherein the focus structure has sloping sidewalls.
24. A detection disc according to clause 23 wherein the focus structure has a V-shaped cross-section.
25. A detection disc according to clause any of clauses 15 to 24, wherein the detection channel has a square or rectangular cross-section.
26. A detection disc according to clause any of clauses 15 to 24, wherein the detection channel has a U-shaped cross section, or may otherwise have a curved base such that the channel has an arc-shaped, inverted-arch-shaped or semi-circular shaped cross-section.
27. A detection disc according to any of clauses 15 to 26, wherein the depth of the focus structure is less than the depth of the channel.
28. A detection disc according to any of clauses 15 to 27, wherein the depth of the channel is twice the depth of the focus structure.
29. A detection disc according to any of clauses 15 to 28, comprising multiple detection channels and multiple focus structures.
30. A detection disc according to clause 29, wherein the multiple detection channels are arranged radially about the disc, and wherein there is at least one focus structure associated with each detection channel.
31. A method of manufacturing a substrate for manufacturing a master for a disc for carrying samples in an apparatus for detection of microscopic objects in a fluid, the substrate having a channel and separate focus structure, wherein the focus structure is a groove, the method comprising:
    providing the substrate having a crystallographic structure;
    forming the channel in the substrate with an orientation independent of the orientation of the crystalline planes; and
    forming the focus structure in the substrate with an orientation aligned with one of the crystalline planes.
32. A method according to clause 31, wherein the substrate is silicon.
33. A method according to clause 32, wherein the channel and focus structure are etched into the (100) plane of the silicon.
34. A method according to clause 33 wherein the focus structure is etched along the {111} plane of the silicon.
35. A method according to any of clauses 31 to 34 wherein the focus structure has a V-shaped cross-section.
36. A method according to any of clauses 31 to 35, wherein the channel is etched to a depth D, and the focus structure is etched to a depth that is less than D.
37. A method according to any of clauses 31 to 36, wherein the focus structure is formed to have a predetermined depth in relation to the depth of the channel.
38. A method according to clause 36 or 37, wherein the focus structure is etched to a depth of D/2.
39. A method according to any of clauses 31 to 38, wherein the focus structure is etched by wet KOH etching.
40. A method according to any of clauses 31 to 39, wherein the channel is etched by DRIE.
41. A method according to any of clauses 31 to 40 comprising providing the substrate with features as described in any of clauses 1 to 14.
42. A method of manufacturing a detection disc for carrying samples in an apparatus for detection of microscopic objects in a fluid, the detection disc comprising injection moulding the detection disc using a production master plate produced using the substrate according to any of clauses 1 to 14.

43. A method of manufacturing a detection disc for carrying samples in an apparatus for detection of microscopic objects in a fluid, the method comprising:
providing a substrate having a crystallographic substrate;
forming the channel in the substrate with an orientation independent of the orientation of the crystalline planes; and
forming the focus structure in the substrate with an orientation aligned with one of the crystalline planes;
using the substrate to produce a production master plate; and
using the production master plate to manufacture the detection disc having a detection channel and a focus structure.

44. A method according to clause 42 or 43, wherein the disc is formed by injection molding or casting.

45. A method of manufacturing a detection disc as clauseed in clauses 42, 43 or 44 comprising providing the disc with features as described in any of clauses 15 to 30.

46. A method of finding a focal plane in an apparatus for detection of microscopic objects in a fluid, wherein the method comprises:
providing an optically transparent substrate having a focus structure, the focus structure comprising a groove with sloping sidewalls provided in a first surface of the substrate;
illuminating the substrate from a second surface, opposed to the first surface;
imaging the focus structure on the first surface using an imaging apparatus, and
focussing the imaging apparatus on the focus structure,
wherein the angle between each sidewall of the focus structure and the first surface is greater than the critical angle of the substrate.

47. A method according to clause 46 wherein the focus structure has a V-shaped cross-section.

48. A method according to clause 46 or 47, further comprising using information about the focal plane found by the imaging apparatus to focus a further, separate, imaging apparatus to the same focal plane.

49. A method according to clause 48, wherein the focussing imaging apparatus is an area detector and the further imaging apparatus is a line detector.

50. A method according to any of clauses 46 to 49, comprising illuminating the detection channel with a line beam, the projection of the line beam being co-linear to the line of the line detector at the imaging plane.

51. A method according to any of clauses 46 to 50 wherein the substrate is a detection disc as described in any of clauses 15 to 30 and the focus structure is a focus structure of the disc.

52. A method of focussing a first imaging apparatus to a focal plane in an apparatus for detection of microscopic objects in a fluid, wherein the method comprises:
imaging a focus structure with a second imaging apparatus,
focussing the second imaging apparatus on the focus structure to find the focal plane; and
focussing the first imaging apparatus to the focal plane to which the second imaging apparatus is focussed.

53. A method according to clause 52, wherein the first imaging apparatus is a line detector, and the second imaging apparatus is an area detector.

54. A method according to clause 52, wherein the first imaging apparatus is an area detector in which a selected line or a selected subset of lines can be read out.

55. A method according to clause 52, wherein a single line detector serves as both the first and second imaging apparatus.

56. A method according to clause 52, wherein a single imaging apparatus where a selected line or a selected subset of lines can be read out serves the purpose of both the first and second imaging apparatus.

57. A method according to any of clauses 52 to 56, wherein the focus structure comprises a groove with sloping sidewalls provided in a first surface of the substrate, and wherein the angle between each sidewall of the focus structure and the first surface is greater than the critical angle of the substrate.

58. A method according to any of clauses 52 to 57, comprising illuminating the detection channel with a line beam, the projection of the line beam being co-linear to the line of the line detector at the imaging plane 59. A method according to any of clauses 52 to 58, wherein the method comprises using a detection disc as described in any of clauses 15 to 30 and the focus structure is a focus structure of the disc.

60. An apparatus for detecting and/or counting microscopic objects comprising:
a detection disc comprising a detection channel for carrying the microscopic objects in a sample fluid and a separate focus structure associated with the detection channel,
a first imaging apparatus for finding a focal plane by focussing on the focus structure; and
a second imaging apparatus for detecting and/or counting the objects in the detection channel, the second imaging apparatus being focussed to the focal plane using information about the focal plane from the first imaging apparatus.

61. An apparatus according to clause 60, wherein the first imaging apparatus is a line detector, and the second imaging apparatus is an area detector.

62. An apparatus according to clause 60, wherein the first imaging apparatus is an area detector in which a selected line or a selected subset of lines can be read out.

63. An apparatus according to clause 62 wherein the area detector is a CMOS area detector 64. An apparatus according to clause 60, wherein a single line detector serves as both the first and second imaging apparatus.

65. An apparatus according to clause 60, wherein a single imaging apparatus where a selected line or a selected subset of lines can be read out serves the purpose of both the first and second imaging apparatus.

66. An apparatus according to any of clauses 60 to 65, wherein the focus structure comprises a groove with sloping sidewalls provided in a first surface of the substrate, and wherein the angle between each sidewall of the focus structure and the first surface is greater than the critical angle of the substrate.

67. An apparatus according to clause any of clauses 60 to 66, comprising a light source for illuminating the detection channel with a line beam, the projection of the line beam being co-linear to the line of the line detector at the imaging plane 68. An apparatus according to clause any of clauses 60 to 67, wherein the detection disc is as described in any of clauses 15 to 30.

69. An apparatus for detecting and/or counting microscopic objects comprising:
   a detection disc comprising a detection channel for carrying the microscopic objects in a sample fluid and a separate focus structure associated with the detection channel,
   a first imaging apparatus for finding a focal plane by focussing on the focus structure;
   a second imaging apparatus for counting the objects in a detection channel, the second imaging apparatus being focussed to the focal plane using information about the focal plane from the first imaging apparatus,
   wherein the focus structure comprises a groove with sloping sidewalls provided in a first surface of the detection disc, and wherein the angle between each sidewall of the focus structure and the first surface is greater than the critical angle of the substrate.
70. An apparatus according to clause 69 wherein the focus structure has a V-shaped cross-section.
71. An apparatus according to clause 69 or 70, comprising a further, separate, imaging apparatus that receives information about the focal plane found by the focussing imaging apparatus and uses this information to focus on the focal plane.
72. An apparatus according to clause 71, wherein the focussing imaging apparatus is an area detector and the further imaging apparatus is a line detector.
73. An apparatus according to clause 72, comprising a light source for illuminating the detection channel with a line beam, the projection of the line beam being co-linear to the line of the line detector at the imaging plane.
74. An apparatus according to any of clauses 69 to 73 wherein the detection disc is as described in any of clauses 15 to 30.
75. A sample processing module for an apparatus for detecting and/or counting microscopic objects, the sample processing module comprising: a carousel for holding a plurality of sample containers; a number of stations for sample processing steps including a filling station for filling the sample containers, a heating station for heating a sample in the sample container; a cooling station for cooling the sample in the sample container; an agitation station for agitating the sample in the sample container; and a purging station for purging the sample from the sample container and passing it to a detection module for analysis of the sample; wherein the heating and cooling stations act on the sample without contact with the sample.
76. A sample processing module according to clause 75, wherein the heating station uses infra-red or heated air to heat the sample.
77. A sample processing module according to clause 75 or 76, wherein each of the filling, heating, cooling and purging stations act without contact between the stations and the sample container held in the carousel.
78. A sample processing module according to clause 75, 76 or 77, wherein the filling station comprises a dispensing nozzle arranged to fill the sample container without contact with the container or carousel.
79. A sample processing module according to any of clauses 75 to 79, wherein the purging station comprises a compressed air source arranged to expel the sample through a hole in the container without contact between the compressed air source and the container or carousel.

What is claimed is:

1. A detection disc for carrying samples in an apparatus for detection of microscopic objects in a fluid, the detection disc including a detection channel and a separate focus structure, wherein the focus structure comprises a groove located outside of the detection channel, said groove comprising sloping sidewalls provided in a first surface of the detection disc, wherein an angle between each sidewall of the groove and the first surface is greater than a critical angle of the detection disc such that when the detection disc is illuminated with a light beam that enters the detection disc from a second surface that is opposite the first surface, light from the light beam is internally reflected by said sidewalls of said groove and light from the light beam is transmitted through a bottom of said groove to a greater extent as compared to said sidewalls to allow for contrast-based focusing between the bottom of the groove and the sidewalls of the groove.

2. A detection disc according to claim 1, wherein the disc is made from a material with refractive index of greater than 1.22.

3. A detection disc according to claim 1, wherein the disc is made from a cyclo olefin polymer.

4. A detection disc according to claim 1 wherein the focus structure has a V-shaped cross-section.

5. A detection disc according to claim 1, wherein a depth of the focus structure is less than a depth of the channel.

6. A detection disc according to claim 1, wherein a depth of the channel is twice a depth of the focus structure.

7. A substrate for use in manufacture of a production master plate for production of a detection disc for carrying samples in an apparatus for detection of microscopic objects in a fluid, the substrate including a channel and a separate focus structure for forming a corresponding channel and a corresponding separate focus structure in the detection disc for focusing an associated imaging apparatus at a predefined imaging plane in the detection disc, wherein the focus structure of the substrate comprises a groove located outside of the channel, said groove comprising sloping sidewalls provided in a first surface of the substrate, wherein an angle between each sidewall of the groove and the first surface of the substrate is greater than a critical angle of the detection disc, and wherein the corresponding focus structure of the detection disc comprises a corresponding groove with sloping sidewalls provided in a first surface of the detection disc with an angle between each sidewall of the corresponding groove and the first surface of the detection disc being greater than the critical angle of the detection disc, such that when the detection disc is illuminated with a light beam that enters the detection disc from a second surface of the detection disc that is opposite the first surface of the detection disc, the light beam is internally reflected by said sidewalls of said corresponding groove and the light beam is transmitted through a bottom of said corresponding groove to a greater extent as compared to said sidewalls of said corresponding groove to allow for contrast-based focusing between the bottom of the corresponding groove and the sidewalls of the corresponding groove.

8. An apparatus for detecting and/or counting microscopic objects comprising:
   a detection disc for carrying samples for detection of microscopic objects in a fluid, the detection disc including a detection channel and a separate focus structure, wherein the focus structure comprises a groove located outside of the detection channel;
   a first imaging apparatus for finding a focal plane by focusing on the focus structure;
   a second imaging apparatus for counting the objects in the detection channel, the second imaging apparatus being focused to a second focal plane using information about the focal plane from the first imaging apparatus, wherein the second focal plane is the same as the focal plane found by the first imaging apparatus or is at an offset from the focal plane found by the first imaging apparatus;

wherein the focus structure groove comprises sloping sidewalls provided in a first surface of the detection disc, and wherein an angle between each sidewall of the focus structure and the first surface is greater than a critical angle of the detection disc such that when the detection disc is illuminated with a light beam that enters the detection disc from a second surface that is opposite the first surface, the light beam is internally reflected by said sidewalls of said groove and the light beam is transmitted through a bottom of said groove to a greater extent as compared to said sidewalls to allow for contrast-based focusing between the bottom of the groove and the sidewalls of the groove.

* * * * *